(12) United States Patent
Wang

(10) Patent No.: US 11,607,406 B2
(45) Date of Patent: Mar. 21, 2023

(54) THERAPEUTICAL METHODS, FORMULATIONS AND NUTRACEUTICAL FORMULATIONS

(71) Applicant: Tianxin Wang, Walnut Creek, CA (US)

(72) Inventor: Tianxin Wang, Walnut Creek, CA (US)

(*) Notice: Subject to any disclaimer, the term of this patent is extended or adjusted under 35 U.S.C. 154(b) by 242 days.

(21) Appl. No.: 16/805,821

(22) Filed: Mar. 1, 2020

(65) Prior Publication Data

US 2020/0197376 A1 Jun. 25, 2020

Related U.S. Application Data

(60) Division of application No. 15/822,205, filed on Nov. 26, 2017, now abandoned, which is a continuation-in-part of application No. 14/824,078, filed on Aug. 12, 2015, now abandoned.

(60) Provisional application No. 62/427,816, filed on Nov. 30, 2016, provisional application No. 62/036,569, filed on Aug. 12, 2014.

(51) Int. Cl.

| | |
|---|---|
| *A61K 31/4375* | (2006.01) |
| *A61K 31/66* | (2006.01) |
| *A61K 31/12* | (2006.01) |
| *A61K 36/38* | (2006.01) |
| *A61K 31/135* | (2006.01) |
| *A61K 31/4525* | (2006.01) |
| *A61K 45/06* | (2006.01) |
| *A61K 36/9066* | (2006.01) |
| *A61K 31/138* | (2006.01) |
| *A61K 31/343* | (2006.01) |
| *A61K 31/7028* | (2006.01) |
| *A61K 31/122* | (2006.01) |
| *A61K 36/66* | (2006.01) |

(52) U.S. Cl.
CPC .......... *A61K 31/4375* (2013.01); *A61K 31/12* (2013.01); *A61K 31/122* (2013.01); *A61K 31/135* (2013.01); *A61K 31/138* (2013.01); *A61K 31/343* (2013.01); *A61K 31/4525* (2013.01); *A61K 31/7028* (2013.01); *A61K 36/38* (2013.01); *A61K 36/66* (2013.01); *A61K 36/9066* (2013.01); *A61K 45/06* (2013.01); *A61K 2300/00* (2013.01)

(58) Field of Classification Search
CPC .. A61K 31/4375; A61K 31/12; A61K 31/122; A61K 31/135; A61K 31/138; A61K 31/343; A61K 31/4525; A61K 31/7028; A61K 36/38; A61K 36/66; A61K 36/9066; A61K 45/06; A61K 2300/00
See application file for complete search history.

(56) References Cited

U.S. PATENT DOCUMENTS

| | | |
|---|---|---|
| 6,974,839 B2 | 12/2005 | Bar-Or |
| 7,105,705 B2 | 9/2006 | Bombardelli |
| 8,158,764 B2 | 4/2012 | Larbouret |
| 9,066,854 B2 | 1/2015 | Lu |
| 9,321,713 B2 | 4/2016 | Shair |
| 2004/0192765 A1 | 9/2004 | Sanchez |
| 2007/0028930 A1 | 2/2007 | Chancellor |
| 2007/0173515 A1 | 7/2007 | Chang |
| 2008/0031980 A1 | 2/2008 | Rodriguez |
| 2008/0262094 A1 | 10/2008 | Bar-Or |
| 2009/0093547 A1 | 4/2009 | Corbitt |
| 2011/0245349 A1 | 10/2011 | Segal |
| 2014/0221497 A1 | 8/2014 | Thor |
| 2014/0350064 A1* | 11/2014 | Chen ............... A61P 19/10 514/415 |
| 2016/0045454 A1 | 2/2016 | Wang |
| 2018/0071269 A1 | 3/2018 | Wang |
| 2018/0098949 A1 | 4/2018 | Wang |

FOREIGN PATENT DOCUMENTS

| | | |
|---|---|---|
| CN | 1899316 B | 3/2011 |
| CN | 102266563 A | 12/2011 |

OTHER PUBLICATIONS

Lu, SciFinder Scholar Abstract Translation (Year: 2012).*
Balayssac et al (Year: 2012).*
Hatzimouratidis et al (Year: 2010).*
Safarinejad (Year: 2007).*
Balayssac (Year: 2012).*
Hatzimouratidis (Year: 2010).*

* cited by examiner

*Primary Examiner* — Jeffrey S Lundgren
*Assistant Examiner* — Ibrahim D Bori

(57) ABSTRACT

Compositions and methods are described for the prevention, treatment, or management of sexual dysfunction, such as premature ejaculation. The method comprises administering an effective amount of tetrahydropalmatine or its derivative or *Rhizoma Corydalis* extract containing composition to a human male on an as-needed basis shortly before sexual activity to delay ejaculation.

9 Claims, No Drawings

THERAPEUTICAL METHODS, FORMULATIONS AND NUTRACEUTICAL FORMULATIONS

CROSS-REFERENCE TO RELATED APPLICATIONS

This application is a divisional application of U.S. patent application Ser. No. 15/822,205 filed on Nov. 26, 2017, which claims priority to U.S. Provisional Patent Application No. 62/427,816 filed on Nov. 30, 2016, which is a Continuation-In-Part application of U.S. patent application Ser. No. 14/824,078 filed on Aug. 12, 2015. The entire disclosure of the prior application is considered to be part of the disclosure of the instant application and is hereby incorporated by reference.

BACKGROUND OF THE INVENTION

Field of the Invention

The invention relates to methods and compositions of delaying ejaculation. In particular, the invention relates to a method of delaying ejaculation by the administration of a tetrahydropalmatine or its derivative or *Rhizoma Corydalis* extract containing composition. The compositions can also be used to treat depression.

Background Information

Premature ejaculation is a debilitating sexual dysfunction. This dysfunction can lead to an inability to enter into, or sustain, relationships and can cause psychological damage to sufferers. Premature ejaculation can also impair reproductive success. Treatments for premature ejaculation include psychological therapies, topical anesthetics, and the use of devices. All of these treatments have significant drawbacks. Psychological therapies benefit only a subset of patients and require specialized therapists who may not be available to all patients. Furthermore, psychological therapies cannot alleviate premature ejaculation resulting from non-psychological causes. Anesthetic agents decrease sensitivity of tissues, thereby diminishing sexual pleasure. Also, topical anesthetics can be transferred to sexual partners and thereby decrease their sensitivity and pleasure as well. With regard to devices, these can be awkward, inconvenient and embarrassing to use. Devices are highly conspicuous and reveal the very condition which the suffering partner may prefer to conceal. Additionally, devices can cause irritation to one or both partners. Methods for treating premature ejaculation by systemic administration of fluoxetine, sertraline, Paroxetine, Dapoxetine and tramadol have been described. However, these drugs may not be effective for all patients, and their side effects can halt treatment or impair patient compliance. Disease states or adverse interactions with other drugs may contraindicate the use of these compounds or require lower dosages that may not be effective to delay the onset of ejaculation.

DESCRIPTION OF THE INVENTIONS AND THE PREFERRED EMBODIMENT

The current invention discloses methods, reagents and pharmaceutical formulations to treat PE (premature ejaculation) or increase the pre-ejaculation time during sexual activity. It also discloses methods, reagents and pharmaceutical formulations to treat erectile dysfunction, cancer, and depression.

One aspect of the current invention provides a low side effect, rapid onset composition to treat premature ejaculation or increase the pre-ejaculation time during sexual activity. It also provide a method to treat premature ejaculation or increase the pre ejaculation time during sexual activity by taking the said formulation orally within 10 hours before intercourse. One example of a preferred composition contains 1~20 mg of escitalopram or 20-100 mg hyperforin, and/or 100-1000 mg *Rhizoma Corydalis* extract and 50~2000 mg of curcumin or curcumin salt (e.g. curcumin sodium salt) or curcumin derivative. Optionally it can further contains 1~20 mg of piperine or turmeric oil. Suitable dosage forms include capsule, liquid capsule, tablet, lozenge, liquid gel, solution (e.g. in 50% ethanol solution) and etc.

The formulation contains one or more antidepressant selected form natural or synthetic SNRI or SSRIs or agomelatine (Valdoxan). The suitable amount of drug used in the formulation is 5%~100% dosage amount of the amount used as antidepressants. Synthetic SNRI is serotonin and norepinephrine reuptake inhibitor, such as venlafaxine, duloxetine. SSRIs are selective serotonin reuptake inhibitors that are generally used antidepressants. Examples of synthetic SSRIs include fluoxetine (Prozac), paroxetine (Paxil), and sertraline (Zoloft), dapoxetine, escitalopram and citalopram.

The formulation also contains curcuminoid polyphenol (curcumin type compound). The suitable amount of curcuminoid used in the formulation is between 20 mg-2000 mg.

Suitable curcumin type compound can be either pure curcumin (diferuloylmethane) or curcuminoid mixture (e.g. that extracted from turmeric, contains approximately 70~80% diferuloylmethane, 10-20% demethoxycurcumin, and 5-10% bisdemethoxycurcumin) or curcumin derivatives. The pure curcumin (diferuloylmethane) performs similar as curcuminoid extracted from turmeric. The terms curcumin, turmeric extract and curcuminoid are used interchangeable in the current invention.

Optionally the composition can further contain 1~20 mg of piperine or chavicine. Piperine, along with its isomer chavicine, is the alkaloid responsible for the pungency of black pepper and long pepper. Optionally turmeric oil (turmerne) can also be added to improve bioavailability of curcumin. One example is Biocurcumax (curcumin mixed with turmeric oil). Optionally it can further contain caffeine 20~200 mg. Optionally it can further contain cGMP-specific phosphodiesterase (PDE5) inhibitor. The suitable dose of PDE5 inhibitor is 20%~150% dosage amount of the amount used in treating erectile dysfunction. Bile acid, chitin or none ionic surfactant such as Poloxamer or Tween (e.g. tween-80) can be added to the formulation to improve the absorption of the drug.

Example of suitable PDE5 inhibitor can be selected from avanafil, lodenafil, mirodenafil, sildenafil, tadalafil, vardenafil, udenafil, zaprinast and icariin. Sildenafil can be added to the formulation at the amount between 10~100 mg. Tadalafil can be added to the formulation at the amount between 1 mg~20 mg. Vardenafil can be added to the formulation at the amount between 1 mg~20 mg.

Suitable amount of antidepressant used in the formulation is Paroxetine 2.5-30 mg, Sertraline 5-100 mg, escitalopram 1-20 mg, citalopram 2-40 mg, dapoxetine 5-60 mg, fluoxetine 5-80 mg, Venlafaxine 5-30 mg, duloxetine 5-60 mg.

In one embodiment, a volunteer took a capsule containing 10 mg of escitalopram, 500 mg of curcuminoid. After 3 hours, the pre ejaculation time was 30 minutes compared with 10 minutes previously without the drug. After 20 hours, the pre ejaculation time was 20 minutes compared with 10 minutes previously without the drug.

In another embodiment, a volunteer took 10 ml 50% ethanol aqueous solution containing 10 mg Escitalopram and 500 mg of curcumin in the form of curcuminoid extract from turmeric. After 1.5 hours, the pre ejaculation time was 30 minutes compared with 10 minutes previously without the drug. After 20 hours, the pre ejaculation time was 20 minutes compared with 10 minutes previously without the drug. In another embodiment, a volunteer took a capsule containing 5 mg of escitalopram, 300 mg of curcuminoid extract from turmeric and 2 mg of piperine. After 3 hours, the pre-ejaculation time was 20 minutes compared with 5 minutes without the drug previously. After 20 hours, the pre-ejaculation time was 20 minutes compared with 5 minutes previously without the drug.

In another embodiment, a volunteer took 5 ml 50% ethanol aqueous solution containing 5 mg of escitalopram, 300 mg of curcumin and 2 mg of piperine. After 1.5 hours, the pre ejaculation time was 20 minutes compared with 5 minutes without the drug previously. After 20 hours, the pre ejaculation time was 20 minutes compared with 5 minutes previously without the drug.

In another embodiment, a volunteer took a capsule containing 10 mg of citalopram, 500 mg of curcumin and 2 mg of piperine. After 3 hours, the pre ejaculation time was 20 minutes compared with 5 minutes without the drug previously. In another embodiment, a volunteer took a capsule containing 1 mg of citalopram, 500 mg of curcumin and 2 mg of piperine. After 3 hours, the pre ejaculation time was 15 minutes compared with 5 minutes without the drug previously. The volunteer also reported improved erection.

It is known that many antidepressants can reduce sex drive and further cause erection dysfunction. The addition of curcuminoid can reduce these side effects and further improve erection.

In another embodiment, a volunteer took a capsule containing 3 mg of escitalopram, 200 mg of curcumin and 30 mg of sildenafil. After 2 hours, the pre ejaculation time was 20 minutes compared with 5 minutes without the drug previously. The volunteer also reported improved erection.

In another embodiment, the formulation is a liquid form contains 5 ml 50% ethanol, 5 mg of escitalopram, 20 mg caffeine, 250 mg of curcumin and 5 mg of vardenafil. The liquid can be taken by the person in need before sexual activity.

In another embodiment, the formulation is a liquid capsule contains 5 mg of escitalopram, 200 mg of curcumin and 30 mg of sildenafil in 50% glycerol, 20% ethanol solution. The capsule can be taken by the person in need 3 hours before the sexual activity.

When volunteers took 20 mg of escitalopram only once orally, significant side effects were observed (stomach irritation, nausea and headache) and no significant changes in pre ejaculation time were observed after 3 hours. When same volunteers took a capsule containing 10 mg of escitalopram+curcumin 500 mg once, much lower side effects were observed and significant increases in pre ejaculation time were observed after 3 hours. When same volunteers took a capsule containing 5 mg of escitalopram+curcumin 500 mg+2 mg of piperine once, no side effects were observed and significant increase in pre ejaculation time were observed after 3 hours comparable to 10 mg of escitalopram+curcumin 500 mg. When the same volunteers took a capsule containing curcumin 500 mg or curcumin 500 mg+2 mg of piperine, no significant changes in pre ejaculation time were observed after 1 hours, 3 hours and 12 hours.

In one embodiment, in repeated experiments a volunteer took a capsule containing 10 mg of paroxetine, 500 mg of curcumin. After 3 hours, the average pre ejaculation time was 25 minutes compared with 10 minutes previously without the drug. The volunteer reported slight side effects (mild nausea).

In one embodiment, in repeated experiments a volunteer took a capsule containing 5 mg of paroxetine, 500 mg of curcumin. After 3 hours, the average pre ejaculation time was 15 minutes compared with 10 minutes previously without the drug. The volunteer reported very slight side effects (very mild nausea).

In another embodiment, in repeated experiments a volunteer took a capsule containing 5 mg of paroxetine, 300 mg of curcumin and 2 mg of piperine. After 3 hours, the average pre ejaculation time was 15 minutes compared with 5 minutes without the drug previously. The volunteer reported no significant side effects. In repeated experiments the same volunteer took a capsule containing 30 mg of paroxetine only and the average pre ejaculation time was 8 minutes after 3 hours compared with 5 minutes without the drug previously. However the volunteer reported significant side effects (stomach irritation, nausea and headache).

In one embodiment, in repeated experiments a volunteer took a capsule containing 20 mg of dapoxetine, 500 mg of curcumin. After 3 hours, the average pre ejaculation time was 20 minutes compared with 10 minutes previously without the drug. The volunteer reported slight side effects (mild nausea).

In another embodiment, in repeated experiments a volunteer took a capsule containing 15 mg of dapoxetine, 300 mg of curcumin and 2 mg of piperine. After 3 hours, the average pre ejaculation time was 20 minutes compared with 5 minutes without the drug previously. The volunteer reported no significant side effects. In repeated experiments the same volunteer took a capsule containing 60 mg of dapoxetine only and the average pre ejaculation time was 20 minutes after 3 hours compared with 5 minutes without the drug previously. However the volunteer reported significant side effects (stomach irritation, nausea and headache).

In one embodiment, in repeated experiments a volunteer took a capsule containing 30 mg of sertraline, 500 mg of curcumin. After 3 hours, the average pre ejaculation time was 15 minutes compared with 5 minutes previously without the drug. The volunteer reported slight side effects (mild nausea). In repeated experiments the same volunteer took a capsule containing 60 mg of sertraline only and no significant increase in pre-ejaculation time was observed after 3 hours; and the volunteer reported significant side effects (stomach irritation, nausea and headache). Only after taking the 60 mg of sertraline once daily for 10 days continuously, the average pre ejaculation time was 10 minutes compared with 5 minutes previously without the drug.

In one embodiment, in repeated experiments a volunteer took a capsule containing 30 mg of duloxetine, 500 mg of curcumin. After 3 hours, the average pre ejaculation time was 10 minutes compared with 5 minutes previously without the drug. The volunteer reported slight side effects (mild nausea). In repeated experiments the same volunteer took a capsule containing 60 mg of duloxetine only and no significant increase in pre-ejaculation time was observed after 3 hours; and the volunteer reported significant side effects (stomach irritation, nausea and headache).

Alternatively, the antidepressant in the above embodiments used can be natural product or natural product extract instead of synthetic SSRI. Preferably the natural antidepressant is St. John's wort extract such as those commercially available as nutraceuticals and medicines used for mood improvement. The preferred dosage of St. John's wort extract used is between 300 mg~3000 mg. Preferably the St. John's wort extract contains at least 3% hypericin, adhyperforin, pseudohypericin, and hyperforin combined weight. In one embodiment, in repeated experiments a volunteer took 1 capsule containing 1000 mg of St. John's wort extract and one capsule containing 1000 mg of curcumin and 5 mg of piperine. After 2 hours, the average pre ejaculation time was 15 minutes compared with 5 minutes previously without the drug. The volunteer reported no side effects. In one embodiment, in repeated experiments a volunteer took 2 capsules each containing 1000 mg of St. John's wort extract and one capsule containing 1000 mg of curcumin and 5 mg of piperine. After 2 hours, the average pre ejaculation time was 20 minutes compared with 5 minutes previously without the drug. The volunteer reported no side effects. In one embodiment, in repeated experiments a volunteer took a mixture of powder containing 1000 mg of St. John's wort extract, 1000 mg of curcumin and 5 mg of piperine. After 2 hours, the average pre ejaculation time was 20 minutes compared with 5 minutes previously without the drug. The commercially available St. John's wort extract contains low amount of hypericin, pseudohypericin, and hyperforin, it can be further concentrated to contain higher amount of hypericin, pseudohypericin, and hyperforin to reduce the amount of drug used accordingly. Furthermore, Morinda officinalis (Medicinal Indianmulberry Root) extract (100 mg~1000 mg) can also be added to the formulation.

The main active agents in St. John's wort extract are hypericin, adhyperforin, pseudohypericin and hyperforin which can be oxidized readily therefore show reduced potency. Curcuminoid is potent antioxidant which protect the active agents in St. John's wort extract from being oxidized therefore improve their potency when being co-formulated and taken together. This is one of the mechanisms that curcuminoid plus St. John's wort extract shows better therapeutical efficacy than using St. John's wort extract alone. Curcuminoid has low bioavailability and most of them keep intact in gastrointestinal (GI) tract, therefore can protect the drug from being oxidized for a longer time in GI tract than other antioxidant that can be absorbed in GI tract readily.

Curcuminoid can also be added to the formulation for other drugs to protect them from being oxidized and increase their potency.

Among hypericin, pseudohypericin and hyperforin in St. John's wort extract, adhyperforin and hyperforin are most potent active substances. Preferably the composition in the current invention contains 5-100 mg hyperforin or adhyperforin or their combination. Most preferably the composition in the current invention contains 10-50 mg hyperforin or adhyperforin or their combination. In one embodiment, in repeated experiments a volunteer took 1 capsule containing 10 mg of hyperforin from concentrated St. John's wort extract, 500 mg of curcumin and 5 mg of piperine. After 2 hours, the average pre ejaculation time was 10 minutes compared with 5 minutes previously without the drug. The volunteer reported no side effects and reported better erection. In another embodiment, a volunteer took 1 capsule containing 10 mg of hyperforin only and after 2 hours the average pre ejaculation time was not changed compared to the time previously without the drug. In another embodiment, in repeated experiments a volunteer took 1 capsule containing 20 mg of mixture of hyperforin and adhyperforin, and 500 mg of curcumin. After 2 hours, the average pre ejaculation time was 15 minutes compared with 5 minutes previously without the drug. The volunteer reported no side effects. In another embodiment, in repeated tests a volunteer took 1 capsule containing 30 mg of hyperforin only. After 2 hours, the average pre ejaculation time was slightly increased to around 8 minutes compared with 5 minutes previously without the drug. However, headache was reported.

Alternatively, hyperforin in the above embodiments can be replaced with hyperforin derivatives/analogues such as those disclosed in U.S. Pat. Nos. 7,105,705 and 9,321,713. Hyperforin derivatives/analogues (e.g. orally taken 10~100 mg) can also increase the pre ejaculation time either used alone or in combination with curcumin. The formulation containing both curcumin and hyperforin derivatives/analogues has better efficacy than using hyperforin derivatives/analogues alone.

Alternatively, Centella asiatica extract can be used alone or added to other embodiments in the current invention to increase the pre ejaculation time and treat depression. Centella asiatica extract's active component contains Centella triterpenic genine, Asiaticoside, Madecassoside, Asiatic & Madecassic acid. Preferably the composition in the current invention as oral formulation contains 100-5000 mg Centella triterpenic genine or Asiaticoside or Madecassoside or Asiatic or Madecassic acid or their combination. In another embodiment, a volunteer took 1 capsule containing 2000 mg of Centella triterpenic genine and after 2 hours the average pre ejaculation time was 10 minutes compared with 5 minutes previously without the drug. In another embodiment, a volunteer took 2000 mg of Centella triterpenic genine, 30 mg hyperforin and 500 mg of curcumin, and after 2 hours the average pre ejaculation time was 15 minutes compared with 5 minutes previously without the drug.

Alternatively, Tramadol can be used in all the above embodiments. When Tramadol is used, antidepressant (e.g. synthetic SSRI or St. John's wort extract) can be omitted or the curcumin can be omitted from the formulation although the combination of all three is also effective. The term "tramadol" is used herein to refer to 2-[(dimethylamino)methyl]-1-(3-methoxyphenyl)-cyclohexanol ("tramadol") and all pharmaceutically-acceptable forms and derivatives of tramadol. In particular, the term includes the N-oxide derivative ("tramadol N-oxide") and the O-desmethyl derivative ("O-desmethyl tramadol"). The term also includes the solvates, polymorphs, and pharmaceutically-acceptable acid addition salts of tramadol and its derivatives. The term further includes all of the stereoisomers of any of the foregoing, including individual stereoisomers (including individual enantiomers) and mixtures of stereoisomers (including the racemates). Preferred dosage is between 5 mg~50 mg.

In one embodiment, in repeated experiments a volunteer took a capsule containing 10 mg of paroxetine, 20 mg of Tramadol. After 3 hours, the average pre ejaculation time was 25 minutes compared with 5 minutes previously without the drug. The volunteer reported slight side effects (mild nausea).

In another embodiment, in repeated experiments a volunteer took a capsule containing 3 mg of escitalopram, 20 mg of Tramadol. After 3 hours, the average pre ejaculation time was 25 minutes compared with 5 minutes previously without the drug. The volunteer reported no side effects. While 20 mg of Tramadol only increase the average pre ejaculation time to 10 min.

In another embodiment, in repeated experiments a volunteer took a capsule containing 500 mg of curcumin, 2 mg of piperine, 20 mg of Tramadol. After 3 hours, the average pre ejaculation time was 25 minutes compared with 5 minutes previously without the drug. The volunteer reported no side effects.

In one embodiment, in repeated experiments a volunteer took a capsule containing 500 mg of curcumin, 2 mg of escitalopram, 10 mg of Tramadol. After 3 hours, the average pre ejaculation time was 25 minutes compared with 5 minutes previously without the drug. The volunteer reported no side effects.

The current invention disclosed that curcuminoid can be co-formulated together or be administered together with other drugs having ejaculation delaying effect to further improve their ejaculation delaying effect, reduce drug dose and reduce side effect. Besides the drugs listed above, other drugs or agents having ejaculation delaying effect can also be used in combination with curcuminoid to boost their efficacy and reduce their side effect and dose. Examples of these agents include but are not limited to morphine and morphine derivatives (e.g. those disclosed in U.S. Pat. No. 8,158,764), Delta opioid receptor agonist (e.g. those disclosed in U.S. patent application Ser. No. 11/696,806) and certain serotonin agonists and antagonists (e.g. those disclosed in U.S. Pat. No. 6,037,360).

The current invention also provides method and formulations containing curcumin and St. John's wort extract to treat depression. The preferred dosage of St. John's wort extract used is between 300 mg~3000 mg. The preferred dosage of curcumin extract used is between 300 mg~3000 mg. A patient suffering depression took one capsule three times daily and each capsule contains St. John's wort extract 300 mg and curcumin 500 mg. After two weeks, the patient report much improved mood and no side effects were observed. Piperine 2-20 mg can also be added to the formulation. Morinda officinalis (Medicinal Indianmulberry Root) extract (100 mg~1000 mg) can also be added to the formulation.

The current invention also provides method and formulations containing curcumin and escitalopram to treat depression. The preferred dosage of curcumin used is between 300 mg~3000 mg. The preferred dosage of escitalopram used is between 5 mg~10 mg. A patient suffering depression took one capsule daily and each capsule contains escitalopram 5 mg and curcumin 500 mg. After two weeks, the patient report much improved mood comparable to taking escitalopram 10 mg daily and no side effects were observed. Piperine 2-20 mg can also be added to the formulation.

The current invention also provides method and formulations containing escitalopram and St. John's wort extract to treat depression. The preferred dosage of St. John's wort extract used is between 300 mg~3000 mg. The preferred dosage of escitalopram used is between 5 mg~10 mg. A patient suffering depression two capsules daily and each capsule contains St. John's wort extract 300 mg and escitalopram 5 mg. After one weeks, the patient report much improved mood comparable to taking escitalopram 20 mg daily. Curcumin 200-500 mg and Piperine 2-20 mg can also be added to each capsule. Furthermore, Morinda officinalis (Medicinal Indianmulberry Root) extract (100 mg~1000 mg) can also be added to the formulation.

In the above methods and formulations to treat depression, the SSRI can be replaced with one synthetic SNRI such as venlafaxine and duloxetine or Valdoxan. The amount of SNRI or Valdoxan used in the formulation can be lower than they being used alone. Normally half daily dose is enough to reach the desired effect.

The current invention also provides formulations containing curcumin as injection dosage to treat diseases such as cancer or Alzheimer. It contains curcumin solid lipid nanoparticles, which can be made by a microemulsion technique such as using microfluidizer at suitable temperature (e.g. at 25-75 degrees C.). It contains curcumin 0.1%-10%, lecithin (e.g. from soybean or egg) 0.2%-20%, optionally surfactant %1~10%, carbohydrate such as lactose, glucose, sugar 1%-20% and water and pH adjusting reagent such as PBS. The mixture can be further lyophilized to improve long term storage stability. When injected to the patient, it provides better bioavailability and better therapeutical effects.

The composition containing both curcumin and St. John's wort extract or composition containing both curcumin and hyperforin can be used for Alzheimer treatment. For example, a capsule containing 500 mg curcumin, Piperine 2 mg and 500 mg St. John's wort extract can be taken orally 3 times a day to treat Alzheimer. In another example, a capsule containing 500 mg curcumin and 30 mg tetrahydrohyperforin can be taken orally 2 times a day to treat Alzheimer. In another example, a capsule containing 500 mg curcumin and 30 mg hyperforin can be taken orally 2 times a day to treat Alzheimer. They can be also be made in injection form to treat Alzheimer.

The current invention also provides a formulation containing curcumin and cordycepin to treat cancer or reduce the side effect of radio/chemotherapy. Preferred curcumin amount is between 300 mg-3 g, and the preferred amount of cordycepin is between 5-100 mg. The cordycepin can be in the form of Cordyceps sinensis extract, Cordyceps militaris extract or those from fermentation as well as synthetic cordycepin. In one embodiment, the formulation is a capsule or tablet contains 500 mg of curcumin, 5 mg of piperine and 20 mg of synthetic cordycepin (or 500 mg of Cordyceps militaris extract which contains 3% cordycepin). A patient takes it three times a day for cancer treatment.

The current invention also provides a formulation containing curcumin and epimedium brevicornu (Horny Goat Weed) extract to treat erectile dysfunction. Preferred curcumin amount is between 300 mg-1 g, and the preferred amount of Epimedium brevicornu extract is between 100 mg-1 g, which can be made from 3-20 g dry Epimedium brevicornu. In one embodiment, the formulation is a capsule or tablet contains 500 mg of curcumin, 500 mg of Epimedium brevicornu extract standardized to contain 10% icariin. Furthermore Maca Extract 75 mg-300 mg can also be incorporated to the formulation. A volunteer took one capsule 3 hours before intercourse showed improved erection and slightly increased ejaculation latency. St. John's wort extract 300 mg~1000 mg can also be added to the capsule/tablet to further increase the ejaculation latency time.

In all the above inventions, suitable curcumin type compound can be either turmeric extract, curcumin (diferuloylmethane) or curcuminoid (e.g. that extracted from turmeric, contains approximately 70~80% diferuloylmethane, 10-20% demethoxycurcumin, and 5-10% bisdemethoxycurcumin) or one or more selected from natural curcumin derivatives including curcumin metabolites including tetrahydrocurcuminoids (e.g. curcumin glucuronide, curcumin sulfate, tetrahydrocurcumin, and hexahydrocurcumin) or synthetic curcumin derivatives such as curcumin mono or di glycoside, curcumin mono or di carboxylic acid ester, curcumin mono or di phosphate. The curcumin (diferuloylmethane) and tetrahydrocurcumin performs similar as curcuminoid extracted from turmeric. Curcumin can be in the form of one or more curcuminoid/curcumin derivatives in complex with micelles, emulsion, nanoparticles, liposome and cyclodextrin such as alpha or beta-cyclodextrin or hydroxypropyl-γ-cyclodextrin and hydroxypropyl-beta-cyclodextrin. Optionally it can further contains 1~20 mg of piperine or 1 mg-200 mg turmeric oil. The above natural products based formulations can be used as nutraceuticals without being approved as drugs.

Rotundine (rotundine) is extracted from the plant Stephania Tetrahydropalmatine L-body, also known as Rotundine or tetrahydropalmatine, palmatine (e.g. L-tetrahydropalmatine, L-THP), an analgesic. It can also be chemically synthesized. Rotundine can be used alone or added to all the formulations in the current invention for PE in effective therapeutical amount (e.g. 10 mg~200 mg) to increase their potency in increasing ejaculation latency. The combination of rotundine with SSRIs (e.g. those used in the previous examples) can provide better delaying ejaculation effect than using them alone. Rotundine can cause user feel sleepy. A medicine that can antagonize hypnotic effect (e.g. Caffeine 10 mg~100 mg and/or Taurine 300 mg~1000 mg) can be added to the formulation.

For example, rotundine can be co-formulated with antidepressant to treat depression and increase ejaculation latency. Example of suitable amount of antidepressant used in the formulation is Paroxetine 2.5-30 mg, Sertraline 5-100 mg, escitalopram 1-20 mg, citalopram 2-40 mg, dapoxetine 5-60 mg, fluoxetine 5-80 mg, Venlafaxine 5-30 mg, duloxetine 5-60 mg. Example of suitable amount of rotundine is between 10~500 mg, preferably between 20~200 mg; for example, 30 mg or 60 mg or 120 mg. In one embodiment, a volunteer took a capsule containing 10 mg of escitalopram, 50 mg of rotundine with optional 20-100 mg caffeine and optional 100-500 mg taurine 1-2 hours before sex. In another embodiment, a volunteer took a capsule containing 10 mg of paroxetine, 30 mg of rotundine and 10 mg of caffeine 2 hours before sex. In one embodiment, a volunteer took a capsule containing 5 mg of paroxetine, 500 mg of curcumin and 60 mg of rotundine 2 hrs before sex. In one embodiment, a volunteer took a capsule containing 5 mg of escitalopram, 500 mg of curcumin, 50 mg caffeine and 30 mg of rotundine 2 hrs before sex. In one embodiment, a volunteer took a capsule containing 500 mg of curcumin and 100 mg of rotundine 2 hrs before sex. In one embodiment, a volunteer took a capsule containing 5 mg of escitalopram, 500 mg of curcumin and 30 mg of rotundine 1 or 2 hrs before sex. Using the above combinations showed better efficacy in increasing ejaculation latency than using SSRI alone or rotundine alone. Natural antidepressant such as St. John's wort extract or its active components such as hyperforin can also be used in combination with rotundine. In one embodiment, a volunteer took a capsule containing 10-50 mg of hyperforin and 30-90 mg of rotundine and 30 mg caffeine with optional 500 mg taurinel or 2 hrs before sex to increase ejaculation latency. The inventor discovered that using rotundine alone (e.g. taken orally 50~200 mg 1 hr before sex) can also increase ejaculation latency, but using it in combination with SSRI or curcumin increases its efficacy. PDE5 inhibitor drugs (e.g. sildenafil) can also be added to the oral formulations such as tablet or capsule.

Alternatively, Melatonin (e.g. 1~20 mg) can also be used instead of rotundine or be used together with above formulations.

Alternatively, *Corydalis* genus such as *Rhizoma Corydalis* (*Corydalis yanhusuo*) extract (e.g. 500~10000 mg such as 5:1 extract using water/ethanol extraction) or Stephania rotunda extract can also be used instead of rotundine in the above embodiments to increase pre ejaculation time or to treat depression alone or in combination with curcumin. The active ingredients of *Rhizoma Corydalis* extract contain alkaloids including corydaline, dl-Tetrahydropalmatine, protopine, L-tetrahydropalmatine, dl-Tetrahydrocladus Alkaloids, L-tetrahydrocannabinol, beta-high-celandine, coptisine, corynebacterium, *corydalis*, berberine, Tetrahydropalmatine Tetrandrine, alkaloid dehydrocorybulbine (DHCB), alkaloids glaucine, palmatine, d-Corydaline, Tetrahydrocolumbamine, *Corydalis* H, *Corydalis* I, *Corydalis* J, *Corydalis* K, *Corydalis* L, α-Allocryptopine, Dehydrocorydaline, d-Corybulbine, Dehydrocorydalmine, Corydalmine, Corypalmine, N-methyltetrahydrocolumbamine, N-methyltetrahydrocoptisine and Norisocorydin. These compounds have similar effect and can be used as purified form or their combination for the current invention. Other tetrahydroprotoberberines (THPB) such as levostepholidine, l-scoulerine and D,L-govadine can also be used in the current invention. Preferably the dosage of the compound listed above or their combination used for the current invention is between 30 mg~3000 mg.

In one embodiment, a volunteer took 5 capsules containing totally 1000 mg of *Rhizoma Corydalis* extract (10:1 concentrate granule, equals to 50 g bulk herb) with optional 20-100 mg caffeine and optional 100-500 mg taurine 0.5-2 hrs before sex. In one embodiment, a volunteer took 2 capsules containing totally 1000 mg of *Rhizoma Corydalis* extract (10:1 concentrate granule, equals to 50 g bulk herb) and 20 mg caffeine 0.5-2 hrs before sex. In one embodiment, a volunteer took 2 capsules containing totally 1000 mg of *Rhizoma Corydalis* extract (10:1 concentrate granule, equals to 50 g bulk herb) and 500 mg St. John's wort extract 0.5-2 hrs before sex. In one embodiment, a volunteer took 50 mL liquid formulation contains 100 mg of rotundine and 100 mg dehydrocorybulbine (DHCB) 2 hrs before sex. The capsules can contains additional curcumin or the like as described previously. In one embodiment, a volunteer took 2 capsules containing totally 1000 mg of *Rhizoma Corydalis* extract (10:1 concentrate granule, equals to 50 g bulk herb) and 500 mg St. John's wort extract and 500 mg curcumin with optional 20-100 mg caffeine and optional 100-500 mg taurine 0.5-2 hrs before sex. In one embodiment, a volunteer took 50 mL liquid formulation contains 100 mg of rotundine and 100 mg dehydrocorybulbine (DHCB) and 30 mg of hyperforin and 30 mg adhyperforin 0.5-2 hrs before sex. In one embodiment, a volunteer took a capsule containing 500 mg of curcumin and 60 mg of rotundine and 60 mg dehydrocorybulbine (DHCB) and 60 mg levostepholidine 2 hrs before sex. All these formulation can cause delayed ejaculation. Extract from danshen root, Panax notoginseng, Radix Angelicae Dahuricae, Rhizoma Cyperi Rotundi, Rhizoma and Ligustici Chuanxiong can also be added to the formulation (e.g. extract equals to 25 g of bulk herb). The active compound from these extract (e.g. 500 mg coumarin of angelicae dahuricae) can also be used instead of the crude extract.

Furthermore, the above formulations can be added with dopamine receptor antagonist in effective therapeutical amount to increase their potency in increasing ejaculation latency. The combination of dopamine antagonist with SSRIs can provide better delaying ejaculation effect than using them alone. Examples of suitable dopamine antagonist include Chlorpromazine, Pimozide, Metoclopramide, Sulpiride, Haloperidol. The dopamine antagonist can be dopamine D3 receptor antagonist such as BP897, CAM89, NGB2904, NGB2849, PG619, CJB090, YQA14, PG01037, RGH188/cariprazine, PG622, FAUC365, ST-198, SB-269652, SB-277011A, SB-414796, R-PG648, PG01037, ABT-925, SR21502, GSK598809, GSK618334, BAK2-66, Buspirone, S33084 and S33138. They can be given to the person in need as an oral formulation 0.5~3 hrs before sex either alone or in combination with other ingredient such as SSRI, hyperforin, curcumin or rotundine as described previously in the current disclosure. The amount used in the formulation to delay ejaculation generally is less than the amount (e.g. 20%~90) of that used in clinics for other indication using dopamine antagonist. For example in one embodiment, a person in need can take 50 mg GSK598809 or GSK618334 1-2 hrs before sex to delay ejaculation; in another embodiment, a person in need can take 30 mg GSK598809 and 1000 mg 2 hrs before sex. In another example, a person in need can take 30 mg GSK598809 and 100 mg L-tetrahydropalmatine 1 hr before sex. In another example, a person in need can take 30 mg GSK598809 and 100 mg L-tetrahydropalmatine and 30 mg caffeine 1 hr before sex. In another example, a person in need can take 30 mg GSK598809 and 10 mg escitalopram 1-2 hrs before sex. In another example, a person in need can take 30 mg GSK598809 and 500 mg curcumin 1-2 hrs before sex. In another example, a person in need can take 30 mg GSK598809 and 20 mg hyperforin 1-2 hrs before sex. In another example, a person in need can take 5 mg Buspirone and 10 mg escitalopram 1-2 hrs before sex. In another embodiment, a person in need can take 3 mg Cariprazine1-2 hrs before sex to delay ejaculation; in another embodiment, a person in need can take 2 mg Cariprazine and 1000 mg 2 hrs before sex. In another example, a person in need can take 3 mg Cariprazine and 100 mg L-tetrahydropalmatine 1 hr before sex. In another example, a person in need can take 3 mg Cariprazine and 100 mg L-tetrahydropalmatine 1 hr before sex. In another example, a person in need can take 3 mg Cariprazine and 10 mg escitalopram 1-2 hrs before sex. In another example, a person in need can take 30 mg Cariprazine and 500 mg curcumin 1-2 hrs before sex. In another example, a person in need can take 3 mg Cariprazine and 20 mg hyperforin 1-2 hrs before sex.

Preferably the dosage form used for the current invention is an orally taken formulation such as capsule, liquid capsule, tablet, lozenge, emulsion, solution and etc, which contains therapeutically effective amount of active ingredient and pharmaceutically acceptable excipients such as starch, cellulose, gelatin and etc, which is well known to the skilled in the art.

What is claimed is:

1. A method of delaying ejaculation in a mammal in need of delaying ejaculation, comprising administering on as needed basis to the mammal, a composition comprising tetrahydropalmatine and a serotonin reuptake inhibitor.

2. The method of claim 1, wherein the mammal is a human male.

3. The method of claim 1, wherein the serotonin reuptake inhibitor is selected from a group consisting of St. John's Wort extract, hyperforin, paroxetine, sertraline, dapoxetine, escitalopram and citalopram.

4. A method of delaying ejaculation in a mammal in need of delaying ejaculation, comprising administering on as-needed basis to the mammal, a composition comprising *Corydalis Yanhusuo* extract.

5. The method of claim 4, wherein the composition further comprises St. John's Wort extract.

6. The method of claim 4, wherein the composition further comprises curcuminoid.

7. The method of claim 1, wherein the tetrahydropalmatine is in the form of *Corydalis Yanhusuo* extract.

8. The method of claim 1, wherein the composition further comprises curcuminoid.

9. The method of claim 1, wherein the amount of tetrahydropalmatine in the composition is between 10 mg and 200 mg.

* * * * *